(12) United States Patent
Li (10) Patent No.: US 9,056,118 B2
(45) Date of Patent: *Jun. 16, 2015

(54) EXTRACT FOR PREVENTING OF TREATING THROMBOTIC DISEASES

(75) Inventor: Zhenguo Li, Mudanjiang (CN)

(73) Assignee: Mudanjiang Youbo Pharmaceutical Co., LTD., Mudanjiang, Heilongjiang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,318

(22) Filed: Jun. 17, 2012

(65) Prior Publication Data

US 2013/0172233 A1 Jul. 4, 2013

Related U.S. Application Data

(63) Continuation-in-part of application No. 12/604,962, filed as application No. PCT/CN2007/070190 on Jun. 26, 2007, now Pat. No. 8,252,340.

(51) Int. Cl.
*A61K 35/62* (2006.01)

(52) U.S. Cl.
CPC ...................................... *A61K 35/62* (2013.01)

(58) Field of Classification Search
CPC .......... A61K 2300/00; A61K 31/4745; A61K 31/555; A61K 38/21; A61K 35/62; A61K 31/282; A61K 45/06; A61K 38/00; A61K 35/646; A61K 35/648; A61K 36/185; A61K 36/25; A61K 36/324; A61K 36/54; A61K 36/65; A61K 31/045

See application file for complete search history.

(56) References Cited

U.S. PATENT DOCUMENTS 4,668,662 A * 5/1987 Tripier .................. 514/14.9
8,252,340 B2 * 8/2012 Li ....................... 424/520

* cited by examiner

*Primary Examiner* — Debbie K Ware (57) ABSTRACT

An extract for preventing or treating thrombotic diseases, particularly, an extract of at least one of leeches and earthworms having a molecular weight of no more than 5,800 daltons is provided, wherein the extract includes 15% to 38% amino acid, 40% to 60% saccharide and 0.3% to 1% hypoxanthine. Processes for preparation, pharmaceutical compositions and uses thereof are also provided. Compared to conventional arts, the extract has safety greatly improved and drug actions maintained and even improved.

9 Claims, 4 Drawing Sheets

EXTRACT FOR PREVENTING OF TREATING THROMBOTIC DISEASES

CROSS REFERENCE OF RELATED APPLICATION

This is a Continuation-In-Parts application of an application having an application Ser. No. 12/064,962 filed on Feb. 27, 2008, now U.S. Pat. No. 8,252,340, which is in a U.S. National Stage under 35 USC 371 of an international application number PCT/CN2007/070190, filed on Jun. 26, 2007.

BACKGROUND OF THE PRESENT INVENTION

1. Field of Invention

The present invention relates to an extract for preventing or treating thrombotic diseases, and more particularly to an extract of leech and earthworm with molecular weight of less than 5,800 daltons, and pharmaceutical composition, processes for preparation and use thereof.

2. Description of Related Arts

As a kind of classic drug of removing blood clot, the Chinese Pharmacopeia records three kinds of leeches—*Whitmania pigra* Whitman, *Hirudo nipponica* Whitman and *Whitmania ac-ranulata* Whitman. Among them, *Whitmania pigra* Whitman is the most widely-used for drug. The main ingredients of leech are protein, polypeptide, amino acids, nucleic acid, enzyme, saccharide, trace elements and etc. The qualitative and quantitative researches about ingredients in leech have been reported for many times. The main methods comprise thin layer chromatography (TLC), high performance liquid chromatography (HPLC), and electrophoresis method. The main micromolecular ingredients in leech are hypoxanthine, xanthine, uracil, uracil riboside and etc. Both Pyrimidine and Purine are unsaturated heterocyclic compounds containing N atoms.

As Chinese traditional medicine, earthworm in the Chinese Pharmacopeia has effects of clearing away heat, calming, getting through arteries and veins, smoothing breathe and diuretic. There are four kinds of earthworm in the Chinese pharmacopeia. They are *Pheretima aspergillum* (E. Perrier), *Pheretima vulgaris* Chen, *Pheretima guillelmi* (Michaelsen) and *Pheretima pectinifera* Michaelsen. Among them, *Pheretima aspergillum* (E. Perrier) also known as Lumbricus is the most widely-used for drug. The main ingredients in earthworm are protein, amino acids, nucleic acid, enzyme, saccharide and etc. The qualitative and quantitative researches about ingredients in earthworm have been reported. The main micromolecular ingredients in earthworm are hypoxanthine and compounds containing N atoms.

Extensive researches of conventional arts indicate that leeches and earthworms definitely contribute to treating thrombotic diseases, and compounds of the polypeptides and the nucleotide fragments isolated from the leeches and the earthworms are well anticoagulant and antithrombotic. A U.S. Pat. No. 5,583,111A, issued on Dec. 10, 1996, discloses anti-thrombotic polypeptides for treatment of thrombotic diseases, which have molecular weights of 14 kilo daltons, 9 kilo daltons and 3 kilo daltons and are isolated from extracts of leeches. A patent of JP1996041098A, issued on Feb. 13, 1996, discloses anti-thrombotic materials of polypeptides and nucleotide fragments obtained from leech extracts. A U.S. Pat. No. 4,668,662A, issued on May 26, 1987, discloses polypeptides extracted and isolated from leeches as an effective anticoagulant in the treatment of the thrombotic diseases. As disclosed from Arch. Pharm. Res., Vol. 20, No. 1, pp 17-23, 1977, powder of earthworms is antithrombotic and anticoagulant and has fibrin-like activity.

A patent of US20050032745A1, issued on Feb. 10, 2005, discloses modified low molecular weight heparin (MLMWH) produced from low molecular weight heparin (LMWH) and having a molecular weight of about 5,000 daltons to 9,000 daltons, preferably 5.400 daltons to 8,000 daltons, and more preferably 5,800 daltons to 7,000 daltons, for the treatment of the thrombotic diseases.

Safety is one of key requirements for injection drugs. Biological macromolecules like polypeptides in animal medicine are always both effective ingredients and harmful ingredients causing a safety problem. Materials possessing immunogenicity often are macromolecule, and the larger molecular weight, the better the immunogenicity. Polypeptides with micromolecule often have no or few immunogenicity. Antigens often are macromolecule because the following probably reasons: (1) The relative molecular weight of antigens are bigger, the superficial specific chemical genes are more, so that the effect of stimulating immunologic cells is better and the immunologic response is stronger; (2) Macromolecular antigens having complex chemical compositions and stable structures can not be destroyed and eliminated easily and can stay in human being's bodies for long time. So they can stimulate immunologic system persistently and immunologic response emerges. Insulin human composed of 51 amino acids (standard molecular weight is 5,800 daltons) is the boundary of distinguishing high molecular weight materials with low molecular weight materials. The high molecular weight materials are controlled strictly in injection.

Extracts of leech and earthworm is the active components in Shuxuetong Injection which possesses high performance and immediate effect in treating cardiovascular and cerebrovascular diseases. Chinese patent applications 03148281.3, 200410101538.8 and 200510000266.7 disclose Shuxuetong Injection and processes for preparation thereof respectively. All content of the applications were referred in the present invention. However, potential hazards exist in injecting and dosing with the injections produced by the conventional arts. For example, when relatively many visible extraneous materials or insoluble microparticals exist and the injections have materials possessing immunogenicity, if the injections are further refined or purified, the anticoagulant and antithrombotic effective ingredients may be eliminated so that drug action may be reduced, while eliminating harmful materials causing untoward reactions including allergy.

Conventional arts only disclose pharmacological actions of the leeches and the earthworms and anticoagulant and antithrombotic active constituent therein. As a kind of animal medicine, the leeches and the earthworms have complex chemical ingredients. The conventional arts fail to provide safe, effective and controllable injections of leeches and earthworms fit for injecting and dosing and processes for preparation thereof, which are applied in treatment of cardiovascular and cerebrovascular diseases, especially in emergency treatment of thromboembolic diseases.

SUMMARY OF THE PRESENT INVENTION

A main object of the present invention is to provide an extract for preventing or treating thrombotic diseases, and more particularly to an extract of leech and earthworm with molecular weight of less than 5,800 daltons, and processes for preparation and use thereof. Compared to conventional arts, the extract of the present invention has safety greatly improved and drug actions maintained and even improved in aspects of preventing blood coagulation and thrombosis;

injections of the present invention can be directly infused or injected without dermal tests and applied in emergency treatment of thromboembolic cardiovascular and cerebrovascular diseases.

Accordingly, in order to accomplish the above object, the present invention is described as follows.

An extract for preventing and treating thrombotic diseases has a molecular weight of less than 5,800 daltons and comprises 15% to 38% amino acid, 40% to 60% saccharine and 0.3% to 1% hypoxanthine based on weight after dehydration and drying.

The extract can be from leech, from earthworm or from a mixture of the two. The extract mixture of leech and earthworm can be a mixture of extract of leech and extract of earthworm, or an extract of the mixture of leech and earthworm.

The leech is *Whitmania pigra* Whitman, *Hirudo nipponica* Whitman or *Whitmania ac-ranulata* Whitman. The earthworm is *Pheretima aspergillum* (E. Perrier), *Pheretima vulgaris* Chen, *Pheretima guillelmi* (Michaelsen) or *Pheretima pectinifera* Michaelsen. In them, dry or fresh *Whitmania pigra* Whitman and *Pheretima aspergillum* (E. Perrier) are preferred.

The extract is obtained by filtration with ultrafiltration membrane or ultrafiltration column which can stay materials with molecular weight of no more than 6,000 daltons (6,000 daltons is preferred). For example, the extract (half-finished product or midbody) which is obtained with conventionally routine method from the raw material (leech and earthworm) is filtrated with the ultrafiltration membrane or ultrafiltration column to produce an extract of leech and earthworm with molecular weight of less than 5,800 daltons.

Preferably, the extract of the present invention is produced by following steps according to process I.

(1) Raw material is cleaned with water for injection or normal saline, steeped at low temperature and filtered. Filtrate and dregs are gained respectively.

(2) Smashed dregs are mixed with filtrate which is obtained in step (1), and homogenate is obtained. The homogenate is frozen and melted repeatedly, then centrifuged, and supernate is obtained.

(3) Supernate which is obtained in step (2) is ultrafiltrated with ultrafiltration membrane or ultrafiltration column which can stay materials with molecular weight of between 10,000-100,000 daltons, and filtrate is obtained.

(4) The filtrate which is obtained in step (3) is ultrafiltrated with ultrafiltration membrane or ultrafiltration column which can stay materials with molecular weight of no more than 6,000 daltons (6,000 daltons is preferred).

If it is necessary, filtration process with ultrafiltration membrane or ultrafiltration column which can stay materials with molecular weight of no more than 6,000 daltons (6,000 daltons is preferred) is repeated. Thermocompression process is handled before filtration if it is necessary, for instance, filtrate is handled at 105-136° C. for 10-45 minutes.

The following steps for preparation are also preferred according to process II:

(1) Raw material is cleaned with water for injection or normal saline and smashed, and then homogenate is obtained. The homogenate is frozen and melted repeatedly, then centrifuged, and supernate is obtained.

(2) The supernate which is obtained in step (1) is ultrafiltrated with ultrafiltration membrane or ultrafiltration column which can stay materials with molecular weight of between 10,000-100,000 daltons, and filtrate is obtained.

(3) The filtrate which is obtained in step (2) is handled with method of ion-exchange chromatography.

(4) The eluent which is obtained in step (3) is filtrated with ultrafiltration membrane or ultrafiltration column which can stay materials with molecular weight of no more than 6,000 daltons after/before process of desalination.

If it is necessary, filtration process with ultrafiltration membrane or ultrafiltration column which can stay materials with molecular weight of no more than 6,000 daltons (6,000 daltons is preferred) is repeated.

Ultrafiltration membrane or ultrafiltration column can be the common kind in the art, such as a hollow fiber ultrafiltration column whose material is polysulfone and having a molecular weight cutoff of no more than 6,000 daltons (6,000 daltons is preferred) and a hollow fiber ultrafiltration column for rough filtration whose molecular weight cutoff is between 10,000 and 100,000 daltons (10,000 daltons or 50,000 daltons is preferred).

The ion exchange column can be a cation exchange column or an anion exchange column. The cation exchange column is selected from a group consisting of CM-sephadex, CM-agarose, CM-cellulose, SP-sephadex, SP-agarose and SP-cellulose. The anion exchange column is selected from a group consisting of DEAE-sephadex, DEAE-agarose, DEAE-cellulose, Q-sephadex, Q-agarose and Q-cellulose.

The extract of the present invention comprises amino acid, saccharide and hypoxanthine.

The amino acid comprises free amino acid and polypeptide amino acid. Preferably, the extract comprises 5% to 20% polypeptide amino acid based on weight after dehydration and drying.

The saccharide comprises monosaccharide and polysaccharide. Preferably, the extract comprises 5% to 20% polysaccharide based on weight after dehydration and drying.

Raw material of leech and earthworm is dry or fresh. Raw material of leech and earthworm are extracted respectively, and extract of leech and extract of earthworm are obtained respectively. Or mixture of raw material of leech and earthworm is extracted, and mixture of extract leech and earthworm is obtained.

The extract is liquid or solid after dehydration and drying.

Another object of the present invention is to provide process for preparation of the extract. The process includes filtration with ultrafiltration membrane or ultrafiltration column which can stay materials with molecular weight of no more than 6,000 daltons (6,000 daltons is preferred). For example, raw material of leech and earthworm is extracted and separated with conventionally routine technology, obtained extract (also called half-finished product or midbody) is filtered with ultrafiltration membrane or ultrafiltration column which can stay materials with molecular weight of no more than 6,000 daltons (6,000 daltons is preferred). Extract of leech and earthworm with molecular weight of less than 5,800 daltons is obtained.

The following steps of process for preparation are preferred.

(1) Raw material is cleaned with water for injection or normal saline, steeped at low temperature and filtered. Filtrate and dregs are gained respectively.

(2) Smashed dregs are mixed with filtrate which is obtained in step (1), and homogenate is obtained. The homogenate is frozen and melted repeatedly, then centrifuged, and supernate is obtained.

(3) Supernate which is obtained in step (2) is ultrafiltrated with ultrafiltration membrane or ultrafiltration column which can stay materials with molecular weight of between 10,000-100,000 daltons, and filtrate is obtained.

(4) The filtrate which is obtained in step (3) is ultrafiltrated with ultrafiltration membrane or ultrafiltration column which can stay materials with molecular weight of no more than 6,000 daltons (6,000 daltons is preferred).

If it is necessary, filtration process with ultrafiltration membrane or ultrafiltration column which can stay materials with molecular weight of not more than 6,000 daltons (6,000 daltons is preferred) is repeated. Thermocompression process is handled before filtration if it is necessary, for instance, filtrate is handled at 105-136° C. for 10-45 minutes.

Determination of molecular weights of materials in the extract of the present invention is accomplished by setting an insulin human having a molecular weight of 5800 daltons as a control and determining a content of giant molecule substance having a molecular weight larger than that of the insulin human.

For example, the content of giant molecule substance is determined with HPLC as follows.

A. Materials and Machines
  1. Material of standard protein molecular weight: insulin human, having a molecular weight of 5,800 daltons, 1 ml/ramus, purchased from the National Institute for the Control of Pharmaceutical and Biological Products of China.
  2. Machines
  Visible ultraviolet spectrophotometer (Japanese Hitachi U-3210)
  High performance liquid chromatograph Water 600
  High performance liquid chromatograph Agilent Hp1100
  3. Reagents
  Trifluoroacetic acid (TFA), chemical pure (Science and Technology University Chemical Industry and Material Institute)
  Acetonitrile, chromatographic pure (Dikma Company)
B. Chromatographic Conditions
  Chromatographic column: gel chromatographic column (TSK GEL 2000 SW×1 7.8 mm*300 mm)
  Mobile phase: trifluoroacetic acid-acetonitrile-water, wherein volume ratio is 0.025:30:70
  Ultraviolet detector: detection wave length of 214±1 nm
  Flow rate: 0.7 ml/min.
C. Determination Suitable quantity sample and insulin human are taken accurately to be mixed with mobile phase respectively, and sample solution and control solution are obtained; Sample solution and control solution are taken accurately to be injected into High performance liquid chromatograph respectively. Chromatogram is recorded. Content of materials with molecular weight of more than 5,800 daltons is calculated by calculating content of materials corresponding to chromatographic peak whose retention time is shorter than retention time of insulin human Content of giant molecular weight in sample is content of materials with molecular weight of more than 5,800 daltons.

Distribution of molecular weights of materials in an extract is also determined with mass spectrometry (MS) as follows.

Suitable quantity of sample (or after desalination) is dissolved in 0.5% TFA solution. Sample solution and base material are mixed together with ratio of 1:1, targeted and dried at room temperature. The base material comprises DHB (2,5-dihydroxy benzoic acid) and CCA (a-cyano-4-hydroxy cinnamic acid).

Determination machine is Autoflex (Bruker Company). MS condition: MALDI-TOF-MS; N2 lasing light emitter whose wave length is 337 nm; linear scanning (length of flying pipe is 1.6 m, accelerating voltage is 20 kv); Ion type is positive ion or negative ion.

Determination result shows that molecular weight of all components in extract of the present invention is less than 5,800 daltons. In other words, there is no material with molecular weight of more than 5,800 daltons. So molecular weight of the extract for preventing or treating thrombotic diseases is no more than 5,800 daltons.

The extract of the present invention comprises amino acid, saccharide and hypoxanthine which are determined as follows.

Determination of the Amino Acid

The amino acid is determined by HPLC in Chinese pharmacopeia 2005 edition $1^{st}$ section appendix VI D.

Chromatographic condition and systematic adaptability test: bulking agent is octadecylsilane chemically bonded silica; mobile phase is A liquid or B liquid, gradient elution, detection wave length is 338 nm and 262 nm, column temperature is 30-40° C.

A liquid: suitable quantity sodium acetate is dissolved in water for injection, and then triethylamine is added. Misce bene; potential hydrogen (PH) is adjusted to neutral, and then tetrahydrofuran (THF) is added.

B liquid: suitable quantity sodium acetate is dissolved in water for injection, and then PH is adjusted to neutral with acetic acid. Mixed liquid of acetonitrile and methanol (1:1) is added, and misce bene.

Amino acid control solution is prepared as follows. Boric acid buffer solution of PH 10.4 is added in control of amino acid, and o-phthalaldehyde and 9-fluorene methyl formate derivative regeant are added. The mixture is stirred uniformly in order to react sufficiently and get o-phthalic acid-9-fluorene methyl formate amino acid which is control liquid.

The extract of the present invention is tested based on following processes and the amino acid thereof is determined by HPLC machine.

General amino acid test solution is prepared by adding suitable quantity of 6 mol/L hydrochloric acid having 1% phenol into suitable quantity of the tested product, bleeding to vacuum to inflate with nitrogen, rapidly sealing up, putting in a constant-temperature drying oven for 22 hours at 110 degrees, adding suitable quantity of 40% sodium hydroxide solution, mixing uniformly to filtrate and handling the filtrate according to the preparation process of the control of the amino acid.

The free amino acid test solution is prepared by handling the tested product according to the preparation process of the control of the amino acid.

The determination is accomplished by injecting precisely adopted amino acid control solution, general amino acid test solution and free amino acid test solution respectively into the HPLC machine and counting with external standard method.

A quantity of the general amino acid minus a quantity of the free amino acid is a quantity of the polypeptide amino acid.

Determination of the Saccharide

General saccharide is determined by precisely adopting suitable quantity of the tested product, putting the adopted tested product into an iodine flask, adding suitable quantity of dilute hydrochloric acid, heating reflux for half an hour, adding phenolphthalein indicator after cooling off, adjusting PH to neutral with sodium hydroxide solution, precisely adding 0.01 mol/L iodine solution, shaking while adding 0.1 mol/L sodium hydroxide solution, shaking uniformly, adding dilute hydrochloric acid after being put in dark, titrating with sodium thiosulfate volumetric solution until a titration end point, adding starch indicator, continuing titration until a disappearance of blue and correcting the titrated results with blank tests.

Monosaccharide is determined by precisely adopting suitable quantity of the tested product, putting the adopted tested product into an iodine flask, precisely adding 0.01 mol/L iodine solution, shaking while adding 0.1 mol/L sodium hydroxide solution, shaking uniformly, adding dilute hydrochloric acid after being put in dark, titrating with sodium thiosulfate volumetric solution until a titration end point, adding starch indicator, continuing titration until a disappearance of blue and correcting the titrated results with blank tests.

A quantity of the general saccharide minus a quantity of the monosaccharide is a quantity of the polysaccharide.

Determination of the Hypoxanthine

The determination of the hypoxanthine also adopts the method of HPLC in Chinese pharmacopeia 2005 edition 1th section appendix VI D. Fixed phase is octadecyl silanebonded silica gel; mobile phase is 0.1% dibasic sodium phosphate solution, and detection wave length is 254 nm. Theoretical plate number is not less than 3,000 according to hypoxanthine.

The hypoxanthine control solution is prepared by precisely measuring suitable quantity of the control of hypoxanthine and dissolving and diluting with water (0.1 mg hypoxanthine/1 ml).

The hypoxanthine is determined by respectively injecting precisely adopted suitable quantity of the tested product and the control solution into the HPLC machine, determining and counting.

In local stimulative test of rabbit, 1 ml extract solution whose concentration is 0.5 g/ml is injected into both leg musculus quadriceps of rabbit. Rabbit is put to death 48 hours later. Both leg quadriceps of rabbit is taken out and cut open. After being observed local stimulative reaction, the musculus quadriceps is put into 10% formaldehyde solution and checked up with routine method of histopathology. Result: there is no congestion and necrosis in leg musculus quadriceps of rabbit with naked eyes. The value is 0 according to reaction grade in stimulative reaction, in other words, there is no evident change. It is confirmed that there is no evident inflammatory reaction through pathology inspection. It also shows that the extract can not initiate evident local simulative reaction.

In blood vessel stimulative test of rabbit, 1 g/kg the extract solution of which concentration is 0.5 g/ml is injected into ear vein of rabbit 1 time/day for 3 days. Pieces of ear of injection position are fixed and checked up with routine method of histopathology. Observe if there is inflammatory reaction in injected vein. Result: it is showed that there is no denatured tissue and necrosis and repeated vein injections of the extract can not initiate evident inflammatory reaction to local veins.

In allergy test of cavia cobaya, 6 healthy cavia cobayas are separated to 2 groups in average. 0.5 ml the extract solution whose concentration is 0.5 g/ml is injected into belly cavity of all cavia cobayas respectively at the 1th, 3th and 5th day. Cavia cobayas of the first group is injected with 1 ml the extract solution at 15th day. Cavia cobayas of the second group is injected with 1 ml the extract solution at 22th day. To observe if there are phenomena of piloerection, anhelation, sneezing, dry vomiting, coughing, gong sound, twitching, atrophy, death and etc in 15 minutes after injection. Result: after all injections are completed, all the phenomena never appear. It shows that the extract can not initiate allergic response to cavia cobaya.

In haemolyticus test of rabbit, there is no hemolytic crisis or erythroagglutination. It shows that the extract can not initiate hemolytic crisis.

So the extract can be used to prepare many kinds of relative praeparatum. The present invention is also related to a kind of drug combination containing the extract. The drug combination is pellet, capsule, drug granules, film agent, patch, coating, suppository, pilula, pulvis, ointment, mistura(fluid by mouth), syrups, tinct, ophthalmus praeparatum, nasal praeparatum, injection, asepsis powder for injection concentrated solution for injection or their sustained-release preparation and controlled release preparation. All the praeparatum is routine drug praeparatum, so they can be obtained with routine drug technology.

The extract or drug combination which can prevent or treat thrombotic diseases can be used to prepare drugs for preventing or treating thrombotic diseases. For example the drug can prevent and treat hyperlipemia, artherosclerosis, myocardial infarction, heartstroke, atherosclerotic infarct of brain, cerebral embolism, thrombosis of vein, lung embolism, pulmonary infarction, thromboangiitis obliterans, arteriosclerosis occlusion, disseminated inravascular coagulation (DIC), surgery complicated by thrombogenesis and thromboembolism, infarction of liver, infarction of kidney, infarction of cholecyst, infarction of mesentery, limbs gangrene, diabetes peripheral neuropathy, retina angiemphraxis, sudden deafness and so on.

The extract for preventing or treating thrombotic diseases of the present invention, which is extracted from the leeches and earthworms under the specific preparation process and has a molecular weight of less than 5,800 daltons, comprises 15% to 38% amino acid, 40% to 60% saccharine and 0.3% to 1% hypoxanthine based on weight after dehydration and drying. The extract comprises active medical components from the leeches and the earthworms which are mixtures of active components of leeches and earthworms and thus is different from antithrombotic compounds of polypeptides or nucleotide fragments isolated from leeches or earthworms as reported in conventional technologies.

The prominent advantage of the extract is that molecular weights of all components of the extract are less than 5,800 daltons and the relatively small molecular weights mean no or few immune reaction. Comparing with conventional extracts of leeches and earthworms, insoluble microparticles in the extract of the present invention are less and smaller, so the extract of the present invention is much safer. Particularly, comparing with the conventional extracts of leeches and earthworms, activity or therapeutical effect of the extract of the present invention is equivalent or better. The extract of the present invention can be used without dermal test, and this can shorten time of saving patients and lessen suffering of patients.

These and other objectives, features, and advantages of the present invention will become apparent from the following detailed description, the accompanying drawings, and the appended claims.

DETAILED DESCRIPTION OF THE PREFERRED EMBODIMENT

Embodiment 1

Equivalent quantity of dry leech and dry earthworm are soaked in normal saline or water for injection so that they can be spread out adequately, then they are washed with normal saline or water for injection repeatedly and put into normal saline or water for injection of 2-4 times volume at 0-4 degree Celsius for 24 hours and filtered, and then filtrate and dregs are preserved for use.

The dregs are pounded to pieces by tissue gravity mill. The filtrate is mixed with colloid mill, and then the mixture is grinded to homogenate whose diameter is less than 0.5 micron. The homogenate is frozen at −15° C. for 15-30 hours and melted at 0-4° C. Then above freezing and melting process is repeated at least 2 times.

The frozen and melted liquid is centrifuged and supernate is obtained. Then the supernate is filtered with ultrafiltration column which can stay materials with molecular weight of more than 50,000 daltons. Obtained filtrate is filtered with ultrafiltration column which can stay materials with molecular weight of more than 10,000 daltons again.

The above finally obtained filtrate is filtered with ultrafiltration column which can stay materials with molecular weight of more than 6,000 daltons. The filtrate is handled at 105-136° C. for 10-45 minutes and filtered with ultrafiltration column which can stay materials with molecular weight of more than 6,000 daltons again. Then extract liquid is obtained.

The extract liquid is dewatered and dried to solid if it is necessary.

Figure 1:
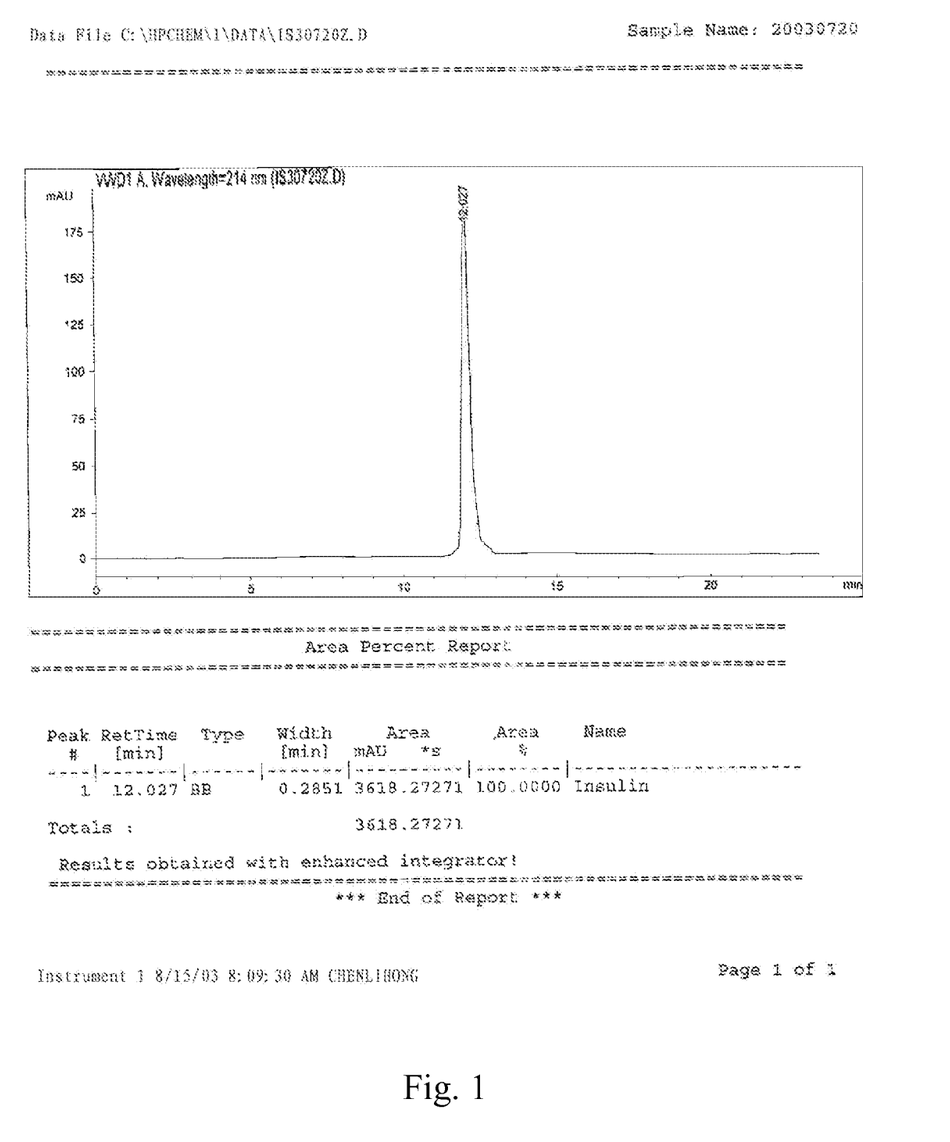
FIG. 1 is a high performance liquid chromatogram detection drawing of insulin human (5,800 daltons).
Figure 2:
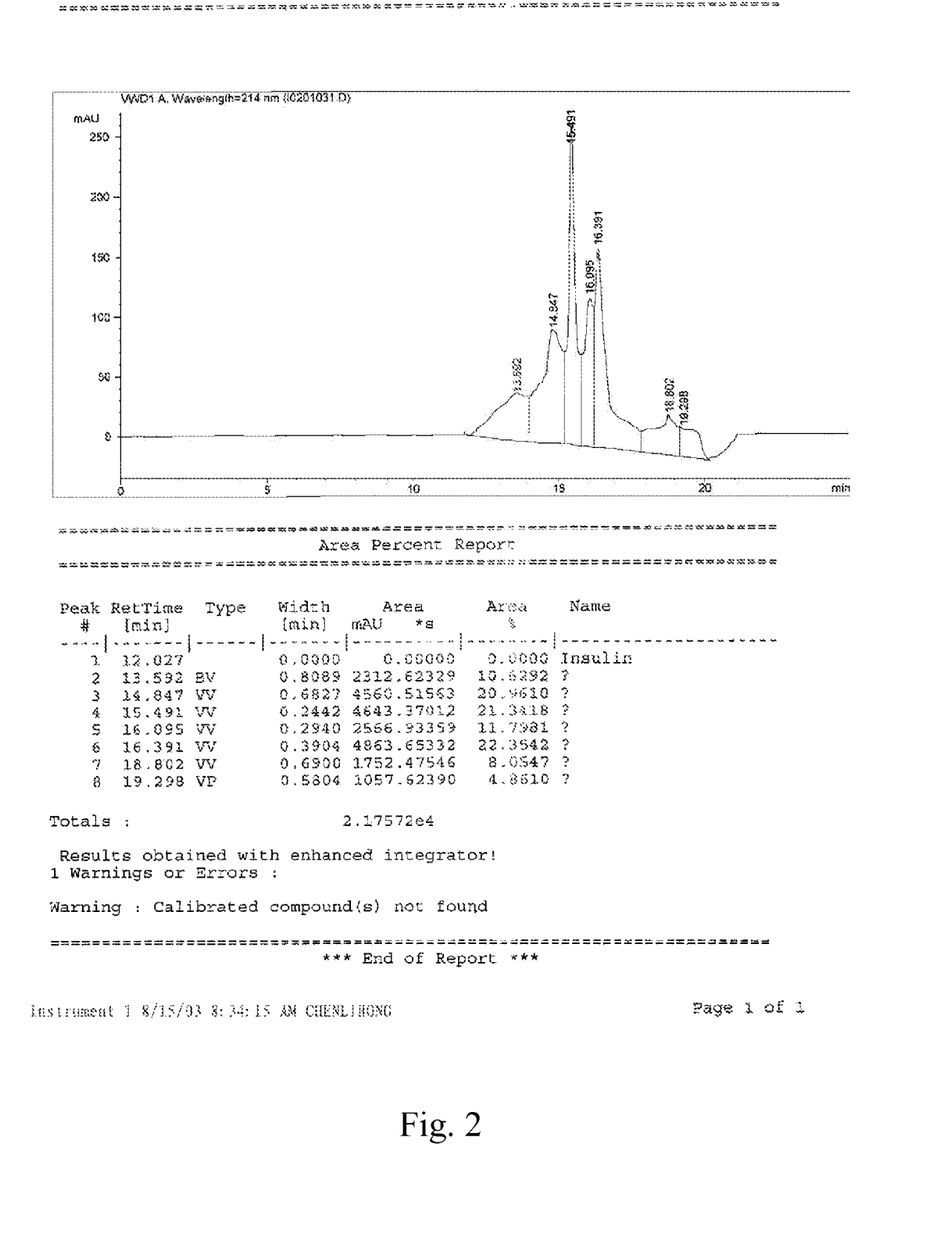
FIG. 2 is a high performance liquid chromatogram detection drawing of extract of leech and earthworm produced by the process I in the present invention.

By the above determination method, the extract liquid comprises amino acid, saccharide and hypoxanthine. By the above HPLC detection, the above extract comprises no material having a molecular weight of more than 5,800 daltons and thus molecular weights of the produced extract are all smaller than 5,800 daltons. FIG. 1 and FIG. 2 show the chromatography detection results. Based on weight and after dehydration and drying, the extract comprises 22.5% amino acid (10.3% polypeptide amino acid based on weight, similarly hereinafter), 45.5% saccharide (12.8% polysaccharide based on weight, similarly hereinafter) and 0.61% hypoxanthine.

All data in FIGS. 1 and 2 is shown in table 1 and 2.

TABLE 1 detection result of insulin human in FIG. 1

| Number of peak | Retention time (min) | Type | Width (min) | Area (mAU) | Percent of area (%) |
|---|---|---|---|---|---|
| 1 | 12.027 | BB | 0.2851 | 3618.27271 | 100 |

Total area: 3618.27271

TABLE 2 detection result of extract in the present invention in FIG. 2

| Number of peak | Retention time (min) | Type | Width (min) | Area (mAU) | Percent of area (%) |
|---|---|---|---|---|---|
| 1 | 12.027 |  | 0.0000 | 0.00000 | 0.0000 |
| 2 | 13.592 | BV | 0.8089 | 2312.62329 | 10.6292 |
| 3 | 14.847 | VV | 0.6827 | 4560.51563 | 20.9610 |
| 4 | 15.491 | VV | 0.2442 | 4643.37012 | 21.3418 |
| 5 | 16.095 | VV | 0.2940 | 2566.93359 | 11.7981 |
| 6 | 16.391 | VV | 0.3904 | 4863.65332 | 22.3542 |
| 7 | 18.802 | VV | 0.6900 | 1752.47546 | 8.0547 |
| 8 | 19.298 | VP | 0.5804 | 1057.62390 | 4.8610 |

Total area: 2.17572e4

Embodiment 2

Equivalent quantity of dry or fresh leech and earthworm are soaked in normal saline or water for injection respectively so that they can be spread out adequately, then they are washed with normal saline or water for injection repeatedly and put into normal saline or water for injection of 2-4 times volume at 0-4° C. for 24 hours and filtered, then filtrate and dregs is preserved for use.

The dregs are pounded to pieces with tissue gravity mill. The filtrate is mixed with colloid mill, and then the mixture is grinded to homogenate of which diameter is less than 0.5 micron. The homogenate is frozen at −15° C. for 15-30 hours and melted at 0-4° C. Then above freezing and melting process is repeated at least 2 times.

The frozen and melted liquid is centrifuged and supernate is obtained. Then the supernate is filtered with ultrafiltration column which can stay materials with molecular weight of more than 50,000 daltons. Obtained filtrate is filtered with ultrafiltration column which can stay materials with molecular weight of more than 10,000 daltons again, and filtrate is obtained.

The above finally obtained filtrate is filtered with ultrafiltration column which can stay materials with molecular weight of more than 6,000 daltons. The filtrate is handled at 105-136° C. for 10-45 minutes and filtered with ultrafiltration column which can stay materials with molecular weight of more than 6,000 daltons again. Then extract liquid is obtained. And extract of leech and extract of earthworm is obtained respectively.

Figure 3:
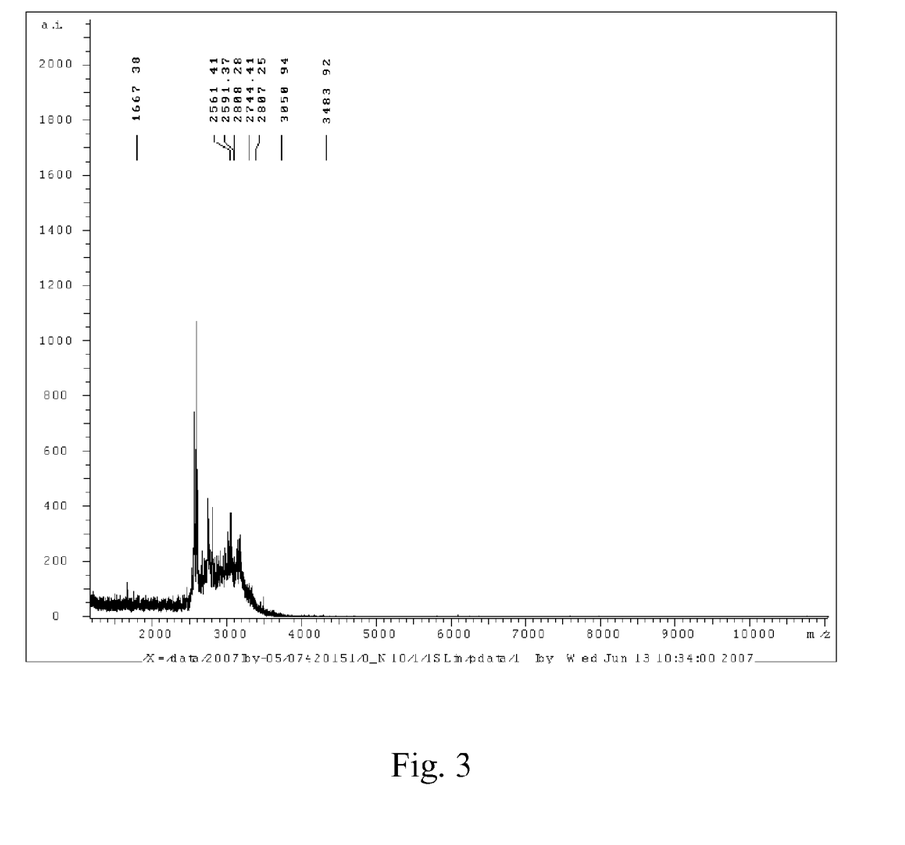
FIG. 3 is a mass spectrometric detection drawing of extract of leech in the present invention, wherein the base material is CCA, and the detection is positive ion.
Figure 4:
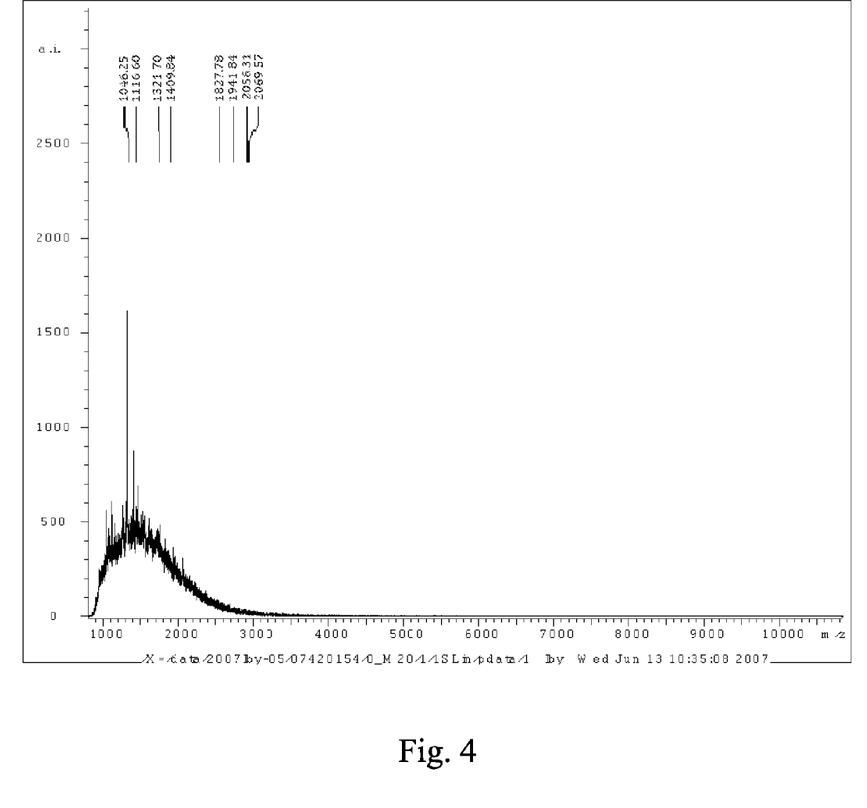
FIG. 4 is a mass spectrometric detection drawing of extract of earthworm in the present invention, the base material is DHB, and the detection is negative ion.

Molecular weight of materials in extract of leech and extract of earthworm is less than 5,800 daltons with above method of MS. The figure is shown in FIGS. 3 and 4. After dehydration and drying and based on weight, the extract of leeches comprises 28.8% amino acid (13.1% polypeptide amino acid), 51.8% saccharide (14.6% polysaccharide) and 0.71% hypoxanthine; after dehydration and drying and based on weight, the extract of earthworms comprises 30.3% amino acid (13.8% polypeptide amino acid), 45.7% saccharide (12.9% polysaccharide) and 0.36% hypoxanthine.

Extract of leech and earthworm is obtained after the two extract are mixed. The mixed extract is added with mannitol and 0.5-1% absorbite in order to eliminate pyrogen, then filtered with micropore film, subpackaged to ampoules, freeze dried and sealed, then the extract of freeze-dry injectable powder is obtained.

Embodiment 3

Equivalent quantity of dry or fresh leech and earthworm are soaked in normal saline or water for injection so that they can be spread out adequately, then they are washed with normal saline or water for injection repeatedly and put into normal saline or water for injection of 2-4 times volume at 0-4° C. for 24 hours and filtered, then filtrate and dregs are preserved for use.

The dregs are pounded to pieces with tissue gravity mill. The filtrate is mixed with colloid mill, and then the mixture is grinded to homogenate of which diameter is less than 0.5 micron. The homogenate is frozen at −15° C. for 15-30 hours and melted at 0-4° C. Then above process is repeated at least 2 times.

The frozen and melted liquid is centrifuged and supernate is obtained. Then the supernate is filtered with ultrafiltration column which can stay materials with molecular weight of more than 50,000 daltons. Obtained filtrate is filtered with ultrafiltration column which can stay materials with molecular weight of more than 10,000 daltons again.

The above finally obtained filtrate is handled at 105-136° C. for 10-45 minutes and filtered with ultrafiltration column which can stay materials with molecular weight of more than 6,000 daltons 2-3 times. Then extract liquid is obtained. After dehydration and drying and based on weight, the extract comprises 23.3% amino acid (10.6% polypeptide amino acid), 49.5% saccharide (13.9% polysaccharide) and 0.58% hypoxanthine.

The liquid is added with 5.4% β-cyclodextrin, stirred uniformly, soaked at 45° C. for 30 minutes and spray dried. And dry powder is obtained.

The dry powder is added with 1.5% silicon dioxide, 0.3% polyvinylpyrrolidone (PVP) and 1% carboxymethyl starch. The mixture is stirred uniformly, granulated and stuffed in hard capsules. And every capsule contains 1 g the dry powder.

Embodiment 4

The extract is obtained with method in embodiment 1.

The extract is added with 6.4% starch, stirred uniformly, dried and sieved. And powder for drug use is contained.

The powder is added with 0.1% gum acacia and 0.1% magnesium stearate, stirred uniformly and stuffed into hard capsules.

Embodiment 5

Influence on Clotting Time of Mouse

20±2 g male mice of Kunming species are separated into 3 groups at random, 16 mice/group. The three groups of mice are injected with 10 ml/kg normal saline, 2.5 g/kg extract of Chinese patent CN03148281.3 and 2.5 g/kg the extract of present invention (embodiment 1) respectively. To take blood in eye sockets of mice 15 minutes later and measure clotting time with method of micrangium. The result is shown in table 3.

TABLE 3 influence to clotting time of mouse ($\bar{x} \pm s$)

| Group | n | Dosage (g/kg) | Clotting time(s) | Extension of clotting time |
|---|---|---|---|---|
| Normal saline | 16 | 10.0 | 70.9 ± 17.9 | — |
| Extract of CN03148281.3 | 16 | 2.5 | 110.5 ± 31.9* | 55.8 |
| Extract of present invention | 16 | 2.5 | 113.7 ± 27.9*# | 60.4 |

Ps:
*$P < 0.01$ comparing with normal saline group;
$P > 0.05$ comparing with extract of CN03148281.3

The result is shown in table 3, Extract of CN03148281.3 can prolong clotting time of mice markedly (Q=5.9637 comparing with normal saline group, P<0.01), and extract of present invention also can prolong clotting time of mice markedly (Q=6.4456 comparing with normal saline group, P<0.01). These two extracts can both prolong clotting time of mice markedly, but there is no distinguished difference between them (Q=0.4819, P>0.05).

Embodiment 6

Influence on Platelet and Platelet Sticking Rate of Rat

1. Influence on Platelet 220-270 g male rats is separated into 3 groups, 10 rats/groups. The three groups of mice are injected with 5 ml/kg normal saline, 1.0 g/kg the extract of present invention and 1.0 g/kg extract of CN03148281.3 respectively. To take blood in eye sockets of mice 15 minutes later and measure platelet with globulimeter. The result is shown in table 4.

2. Influence on Platelet Sticking Rate 220-270 g male rats is separated to 3 groups, 10 rats/groups. The three groups of mice are injected with 5 ml/kg normal saline, 1.0 g/kg the extract of present invention and 1.0 g/kg extract of CN03148281.3 respectively. To take blood in eye sockets of mice 15 minutes later and measure platelet this is number of platelet before sticking. 1.5 ml blood is put into tube in which there is 0.3 ml 3.8% natrium citricum solution. To stirred uniformly and take 1 ml mixture into a silicon tube ring. The ring is put into vitro thrombogenesis-platelet adhesion reaction machine and run for 5 minutes with speed of 17 turns/minute. To take blood to measure number of platelet as number of platelet after sticking and calculate platelet sticking rate. The result is shown in table 4. Calculation method of platelet is as follows:

sticking rate(%)=(number of platelet before sticking-number of platelet after sticking)/number of platelet before sticking×100%

TABLE 4 influence to platelet and platelet sticking rate of rat

| group | n | Dosage (g/kg) | Platelet number ($10^3/mm^3$) | Reduction of platelet (%) | platelet sticking rate (%) |
|---|---|---|---|---|---|
| Normal saline | 10 | 5.0 | 171.1 ± 45.6 | — | — |
| Extract of CN03148281.3 | 10 | 1.0 | 148.5 ± 22.1* | 12.2 | 37.5 ± 13.5 |
| Extract of present invention | 10 | 1.0 | 131.4 ± 17.2**# | 15.2 | 32.0 ± 12.9# |

Ps:
*$P < 0.05$,
**$P < 0.01$ comparing with normal saline group;
$P > 0.05$ comparing with extract of CN03148281.3

The result is shown in table 4: extract of CN03148281.3 can lower platelet number of normal rats markedly (Q=2.9260, P<0.05 comparing with normal saline group, P<0.01), extract of present invention also can lower platelet number of normal rats markedly (Q=5.1399, P<0.01 comparing with normal saline group, P<0.01). These two extract can both lower platelet number of normal rats, but there is no distinguished difference between them (Q=2.2139, P>0.05). It is shown that extract of present invention and extract of CN03148281.3 can both lower platelet number and platelet sticking rate and decrease formation of thrombus.

Embodiment 7

Detection of Visible Extraneous Material and Insoluble Microparticle

Extract of leech and earthworm (called extract of CN03148281.3) is obtained with dry leech and dry earthworm referring to method in CN03148281.3.

1 detection of visible extraneous material: visible extraneous materials in extract of present invention (embodiment 1) and extract of CN03148281.3 are detected respectively referring to Chinese Pharmacopeia (2005 edition) praeparatum general notice injection rule. The result is shown in table 5.

TABLE 5 detection result of visible extraneous material

| Item sample | Qualified rate of lamp detection | Short and small fiber |
|---|---|---|
| extract of present invention | 92.7% | 3.9% |
| extract of CN03148281.3 | 63.7% | 28.5% |

The result shows that there is novel difference between extract of present invention and extract of CN03148281.3 in visible extraneous material. Qualified rate of lamp detection and short and small fiber of extract of present invention are better than these of extract of CN03148281.3. So extract of present invention is safer.

2 detection of insoluble microparticle: insoluble microparticle in extract of present invention (embodiment 1) and extract of CN03148281.3 are detected respectively referring to Chinese Pharmacopeia (2005 edition) praeparatum general notice injection rule. The result is shown in table 6.

TABLE 6 detection result of insoluble microparticle

| Item sample | Microparticle of more than 10 um (average value/ramus) | Microparticle of more than 25 um (average value/ramus) |
|---|---|---|
| extract of present invention | 196/ramus | 65/ramus |
| extract of CN03148281.3 | 250/ramus | 110/ramus |

The result shows that there is novel difference between extract of present invention and extract of CN03148281.3 in insoluble microparticle. Insoluble microparticle number of extract of present invention is much smaller than that of extract of CN03148281.3. So extract of present invention is safer.

Above results shows that there is no evident difference in drug action between extract of present invention and extract of CN03148281.3, and the former is better than the latter in some indexes. In other words, extract of present is much safer with same drug activity.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An extract for treating thrombotic diseases, produced by a process comprising following steps of:
   (1) cleaning a raw material comprising leeches and earthworms, with water for injection or normal saline, steeping at low temperature and filtrating to gain filtrate and dregs respectively;
   (2) mixing smashed dregs with filtrate which is obtained in said step (1) to produce homogenate, freezing and melting repeatedly and centrifuging the homogenate to obtain supernate;
   (3) ultrafiltrating the supernate which is obtained in said step (2) with ultrafiltration membrane or ultrafiltration column which is able to stay materials with molecular weights of between 10,000 and 100,000 daltons to obtain filtrate;
   (4) filtrating the filtrate which is obtained in said step (3) with ultrafiltration membrane or ultrafiltration column which is able to stay materials with molecular weight of no more than 6,000 daltons; and
   (5) obtaining the extract by High Performance Liquid Chromatography (HPLC), said extract has components having molecular weights less than 5,800 daltons and comprises 15% to 38% amino acid, 40% to 60% saccharine and 0.3% to 1% hypoxanthine based on weight after dehydration and drying.

2. The extract as recited in claim 1, wherein said step (4) comprises thermocompressing before filtration, wherein the filtrate is handled at 105-136° C. for 10 to 45 minutes.

3. The extract as recited in claim 2, wherein the leeches and the earthworms are mixed after being respectively extracted or extracted after being mixed together; the leeches and the earthworms are respectively dry or fresh.

4. A drug composition comprising the extract as recited in claim 2 as active ingredient.

5. The drug composition, as recited in claim 4, wherein said drug composition is a member selected from a group consisting of pellet, capsule, drug granules, film agent, patch, coating, suppository, pilula, pulvis, ointment, mistura, syrups, tinct, ophthalmus praeparatum, nasal praeparatum, injection, asepsis powder for injection concentrated solution for injection and sustained-release preparation and controlled release preparation.

6. A process for treating thrombotic diseases, said diseases comprising hyperlipemia, artherosclerosis, myocardial infarction, heartstroke, atherosclerotic infarct of brain, cerebral embolism, thrombosis of vein, lung embolism, pulmonary infarction, thromboangiitis obliterans, arteriosclerosis occlusion, disseminated intravascular coagulation (DIC), surgery complicated by thrombogenesis and thromboembolism, infarction of liver, infarction of kidney, infarction of cholecyst, infarction of mesentery, limbs gangrene, diabetes peripheral neuropathy, retina angiemphraxis and sudden deafness in a subject, said process comprising a step of administering a therapeutically effective amount of a drug comprising the extract as recited in claim 1 to the subject.

7. An extract for treating thrombotic diseases, produced by a process comprising following steps of:
   (1) cleaning a raw material comprising leeches and earthworms, with water for injection or normal saline, steeping at low temperature and filtrating to gain filtrate and dregs respectively;

(2) mixing smashed dregs with filtrate which is obtained in said step (1) to produce homogenate, freezing and melting repeatedly and centrifuging the homogenate to obtain supernate;
(3) ultrafiltrating the supernate which is obtained in said step (2) with ultrafiltration membrane or ultrafiltration column which is able to stay materials with molecular weights of between 10,000 and 100,000 daltons to obtain filtrate;
(4) filtrating the filtrate which is obtained in said step (3) with ultrafiltration membrane or ultrafiltration column which is able to stay materials with molecular weight of 6,000 daltons; and
(5) obtaining the extract by High Performance Liquid Chromatography (HPLC), said extract has components having molecular weights less than 5,800 daltons and comprises 15% to 38% amino acid, 40% to 60% saccharine and 0.3% to 1% hypoxanthine based on weight after dehydration and drying.

8. The extract as recited in claim 7, wherein said step (4) comprises thermocompressing before filtration, wherein the filtrate is handled at 105-136° C. for 10 to 45 minutes.

9. The extract as recited in claim 8, wherein the leeches and the earthworms are mixed after being respectively extracted or extracted after being mixed together; the leeches and the earthworms are respectively dry or fresh.

* * * * *